US012582298B2

(12) United States Patent
Zhou

(10) Patent No.: US 12,582,298 B2
(45) Date of Patent: Mar. 24, 2026

(54) CONTROL ELEMENT FOR ENDOSCOPE, SELF-LOCKING DEVICE, HANDLE, AND ENDOSCOPE

(71) Applicant: HUNAN VATHIN MEDICAL INSTRUMENT CO., LTD., Xiangtan (CN)

(72) Inventor: Zhenhua Zhou, Xiangtan (CN)

(73) Assignee: HUNAN VATHIN MEDICAL INSTRUMENT CO., LTD., Xiangtan (CN)

( * ) Notice: Subject to any disclaimer, the term of this patent is extended or adjusted under 35 U.S.C. 154(b) by 0 days.

(21) Appl. No.: 19/223,051

(22) Filed: May 30, 2025

(65) Prior Publication Data

US 2025/0288191 A1 Sep. 18, 2025

Related U.S. Application Data

(63) Continuation-in-part of application No. PCT/CN2023/128099, filed on Oct. 31, 2023.

(30) Foreign Application Priority Data

Nov. 30, 2022 (CN) .......................... 202211516724.2

(51) Int. Cl.
*A61B 1/005* (2006.01)
*A61B 1/00* (2006.01)

(52) U.S. Cl.
CPC .................................. *A61B 1/0052* (2013.01)

(58) Field of Classification Search
CPC .............. A61B 1/0052; A61B 1/00066; A61B 1/00042
See application file for complete search history.

(56) References Cited

U.S. PATENT DOCUMENTS 6,188,158 B1 2/2001 DeLuca et al.
2011/0088498 A1 4/2011 Ettwein et al.
(Continued)

FOREIGN PATENT DOCUMENTS

CN 101227814 A 7/2008
CN 104936502 A 9/2015
(Continued)

*Primary Examiner* — Anh Tuan T Nguyen
*Assistant Examiner* — Rynae E Boler
(74) *Attorney, Agent, or Firm* — Bayramoglu Law Offices LLC

(57) ABSTRACT

A control element for an endoscope includes a mounting base and an elastic member. The mounting base is provided with an avoidance area; the avoidance area is a hole or groove penetrating through the mounting base; the elastic member is disposed corresponding to the avoidance area; one end of the elastic member is connected to the mounting base, and the other end of the elastic member is a free end; a projection of the elastic member on a plane where the mounting base is located covers a part of the avoidance area; and the elastic member is provided with a first protrusion. The control element improves the control element corresponding to a leaf spring by redesigning the deformable portion of the elastic member. The control element increases the upper limit for the deformation amount of the elastic member while reducing resistance corresponding to unit deformation amount of the elastic member.

12 Claims, 8 Drawing Sheets

(56)  References Cited

U.S. PATENT DOCUMENTS

| | | | | |
|---|---|---|---|---|
| 2021/0212552 A1* | 7/2021 | Uehara | ............. | A61B 1/00042 |
| 2021/0315445 A1* | 10/2021 | Wilder | ................ | A61B 1/0058 |
| 2023/0151653 A1* | 5/2023 | Iwasaki | ............... | A61B 1/0052 |
| | | | | 70/77 |
| 2023/0172439 A1* | 6/2023 | Lund | ................. | A61B 1/00042 |
| | | | | 600/148 |

FOREIGN PATENT DOCUMENTS

| | | | | | | |
|---|---|---|---|---|---|---|
| CN | 206007206 | U | * | 3/2017 | | |
| CN | 111202488 | A | * | 5/2020 | ......... | A61B 1/00042 |
| CN | 111803009 | A | | 10/2020 | | |
| CN | 114947700 | A | * | 8/2022 | ......... | A61B 1/00066 |
| CN | 115153394 | A | | 10/2022 | | |
| CN | 116269150 | A | | 6/2023 | | |
| DE | 4012808 | A1 | | 5/1991 | | |
| DE | 102016012955 | A1 | | 5/2018 | | |
| WO | 2021213600 | A1 | | 10/2021 | | |

* cited by examiner

100

100

CONTROL ELEMENT FOR ENDOSCOPE, SELF-LOCKING DEVICE, HANDLE, AND ENDOSCOPE

CROSS REFERENCE TO THE RELATED APPLICATIONS

This application is the continuation-in-part application of International Application No. PCT/CN2023/128099, filed on Oct. 31, 2023, which is based upon and claims priority to Chinese Patent Application No. 202211516724.2, filed on Nov. 30, 2022, the entire contents of which are incorporated herein by reference.

TECHNICAL FIELD

The present disclosure relates to the technical field of endoscopy, and in particular to a control element for an endoscope, a self-locking device, a handle, and an endoscope.

BACKGROUND

At present, endoscopes are widely used in the medical field. During endoscopic procedures, medical personnel control the position of the lens of the endoscope in the human body through a toggle handle and utilize a self-locking device to assist in endoscope manipulation.

Existing self-locking devices for endoscopes, such as the one disclosed in Chinese patent application CN111202488A, employ a leaf spring to determine completion of the switching control between locked and unlocked states. However, in practical use, medical personnel encounter excessive resistance during switching control between locked and unlocked states, resulting in operational inconvenience.

SUMMARY

An objective of the present disclosure is to solve the above-mentioned problems existing in the prior art, and mainly includes the following four aspects.

A first aspect of the present disclosure provides a control element for an endoscope, including a mounting base and an elastic member, where the mounting base is provided with an avoidance area; the avoidance area is a hole or groove penetrating through the mounting base; the elastic member is disposed corresponding to the avoidance area; one end of the elastic member is connected to the mounting base, and the other end of the elastic member is a free end; a projection of the elastic member on a plane where the mounting base is located covers a part of the avoidance area; and the elastic member is provided with a first protrusion.

Furthermore, the mounting base is provided with a mounting hole.

Furthermore, the elastic member is integrated with the mounting base.

Furthermore, the elastic member includes a first section and a second section; the second section serves as the free end; the second section is connected to the mounting base via the first section; the first protrusion is disposed on the second section; the first section is located on an extension line of the second section; and alternatively, the first section and the second section form an L-shaped structure.

Furthermore, the first protrusion includes a first inclined surface and a second inclined surface; the second inclined surface has a greater slope than the first inclined surface; and the second inclined surface is located between the first inclined surface and the first section.

Furthermore, the second section further includes a first flat portion connected to the first inclined surface and a second flat portion connected to the second inclined surface; and the first flat portion is connected to the first section.

Furthermore, the elastic member further includes a third section; one end of the second section is connected to the mounting base via the first section, and the other end of the second section is connected to the mounting base via the third section; and the elastic member has a U-shaped structure.

Furthermore, the first section is provided with a second protrusion; and/or the third section is provided with a third protrusion.

A second aspect of the present disclosure provides a self-locking device for an endoscope, including a driving gear, a driven gear, a flap, and the above-mentioned control element, where the driven gear is located between the driving gear and the flap; the driving gear and the driven gear are coaxially arranged; the flap is slidably connected to the driven gear; a sliding stroke between the flap and the driven gear includes a first positional state and a second positional state; in the first positional state, the driving gear is separated from the driven gear; in the second positional state, the driving gear is engaged with the driven gear; the control element is disposed on a side wall of the driven gear adjacent to the flap; the flap is provided with a limiting member; and the limiting member is configured to cooperate with the elastic member to achieve locking of the first positional state and/or the second positional state.

Furthermore, the first protrusion is configured to cooperate with the limiting member to achieve locking of the first positional state; and the limiting member is configured to cooperate with the elastic member to achieve locking of the second positional state.

Furthermore, the driven gear is provided with a protrusion; the protrusion is provided with a sliding groove; a slider matching the sliding groove is disposed in the sliding groove; the slider is connected to the flap; the driving gear and the driven gear are coaxially arranged on a rotating shaft; the driven gear is slidably connected to the rotating shaft along an axial direction; the driving gear is coaxially rotatably connected to the rotating shaft; and an angle between the sliding groove and a central axis of the rotating shaft is acute.

Furthermore, the protrusion is disposed on the side wall of the driven gear adjacent to the flap; and the protrusion passes through the avoidance area.

Furthermore, the side wall of the driven gear adjacent to the flap is provided with a mounting post matching with the mounting hole.

A third aspect of the present disclosure provides a handle for an endoscope, including a housing, a lever, and the above-mentioned self-locking device, where the driving gear and the driven gear are disposed inside the housing; the lever is connected to the flap; and at least a portion of the lever is disposed outside the housing.

A fourth aspect of the present disclosure provides an endoscope, including the above-mentioned self-locking device or handle.

Compared with the prior art, the present disclosure has at least the following technical effects.

The present disclosure improves the control element corresponding to the leaf spring. The present disclosure redesigns the deformable portion of the elastic member and increases the upper limit for the deformation amount of the elastic member, reducing resistance corresponding to unit deformation amount generated by the elastic member. Meanwhile, the present disclosure enlarges the deformation space for elastic deformation of the elastic member, reducing resistance during elastic deformation of the elastic member. Therefore, medical personnel can easily and quickly complete state switching control, improving operational convenience of the endoscope.

BRIEF DESCRIPTION OF THE DRAWINGS

To describe the technical solutions in the embodiments of the present disclosure more clearly, the following briefly introduces the drawings required for describing the embodiments or the prior art. Apparently, the drawings in the following description show merely some embodiments of the present disclosure, and persons of ordinary skill in the art may still derive other drawings from these drawings without creative efforts.

REFERENCE NUMERALS

Figure 1:
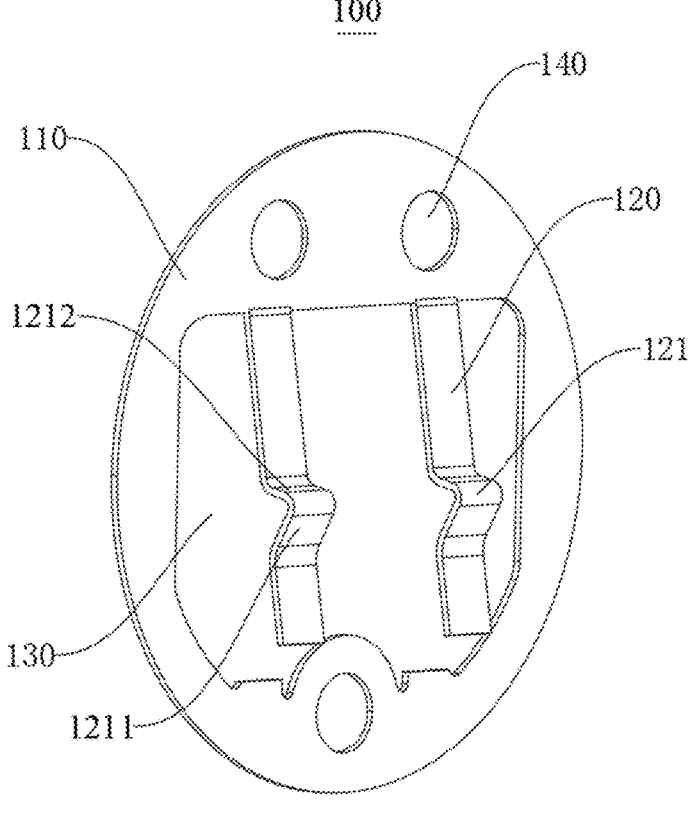
FIG. 1 is a three-dimensional structural schematic diagram of a control element according to the present disclosure.

100. control element; 110. mounting base; 120. elastic member; 121. first protrusion; 1211. first inclined surface; 1212. second inclined surface; 122. second protrusion; 123. third protrusion; 126. first section; 127. second section; 1271. first straight portion; 1272. second straight portion; 128. third section; 130. avoidance area; 140. mounting hole; 210. driving gear; 220. driven gear; 221. protrusion; 222. sliding groove; 223. mounting post; 224. slider; 230. flap; 231. limiting member; 240. lever; 250. rotating shaft; and 40. housing.

DETAILED DESCRIPTION OF THE EMBODIMENTS

The following description provides many different embodiments or examples for implementing different features of the present disclosure. The elements and arrangements described in the following specific examples are only intended to concisely express the present disclosure, and are only for illustration purposes, rather than to limit the present disclosure.

In order to make the objectives, technical solutions, and advantages of the embodiments of the present disclosure clearer, the technical solutions in the embodiments of the present disclosure will be clearly and completely described below in conjunction with the drawings in the embodiments of the present disclosure. Obviously, the described embodiments are some, rather than all of the embodiments of the present disclosure. On the basis of the embodiments of the present disclosure, all other embodiments obtained by a person of ordinary skill in the art without making creative efforts shall fall within the protection scope of the present disclosure. Therefore, the detailed description of the embodiments of the present disclosure in the drawings is not intended to limit the protection scope of the present disclosure, but merely represent the selected embodiments of the present disclosure. On the basis of the embodiments of the present disclosure, all other embodiments obtained by a person of ordinary skill in the art without making creative efforts shall fall within the protection scope of the present disclosure.

In the present disclosure, unless otherwise clearly specified, the terms "installation", "interconnection", "connection" and "fixation" etc. are intended to be understood in a broad sense. For example, the "connection" may be a fixed connection, removable connection or integral connection; may be a mechanical connection or electrical connection; may be a direct connection or indirect connection using a medium; and may be a communication or interaction between two elements. Those of ordinary skill in the art may understand specific meanings of the above terms in the present disclosure based on a specific situation. In addition, the terms such as "first", "second", and "third" are used only for the purpose of description and cannot be understood to indicate or imply relative importance.

In the present disclosure, unless otherwise expressly specified, when it is described that a first feature is "above" or "under" a second feature, it may indicate that the first feature is in direct contact with the second feature, or that the first feature and the second feature are not in direct contact with each other but are in contact via another feature between them. Moreover, "a first feature is above and on a second feature" includes "the first feature is directly above or obliquely above the second feature" or simply means that "the first feature is higher than the second feature". "A first feature is under and below a second feature" includes "the first feature is directly under or obliquely under the second feature" or simply means that "the first feature is lower than the second feature".

In addition, in the present disclosure, for the convenience of describing and understanding the positional relationship between components, "proximal end" and "distal end" refer to proximal and distal positions of a structure for in-vivo operation in an operating environment. For the same component, "proximal end" and "distal end" refer to the relative rather than absolute positional relationship of the component. Therefore, the understanding of "proximal end" and "distal end" should be based on the principles of the present disclosure, without deviating from the essence of the present disclosure.

Embodiment 1

Figure 2:
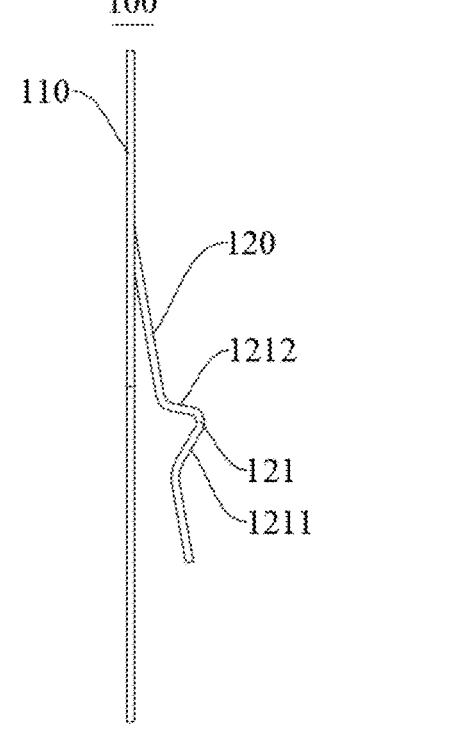
FIG. 2 is a side view of the control element according to the present disclosure.
Figure 3:
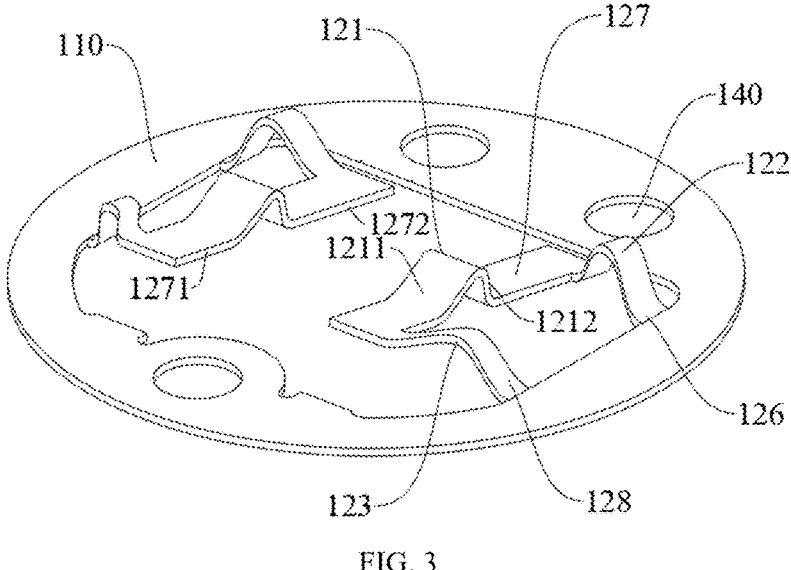
FIG. 3 is a second structural schematic diagram of the control element according to the present disclosure.
Figure 4:
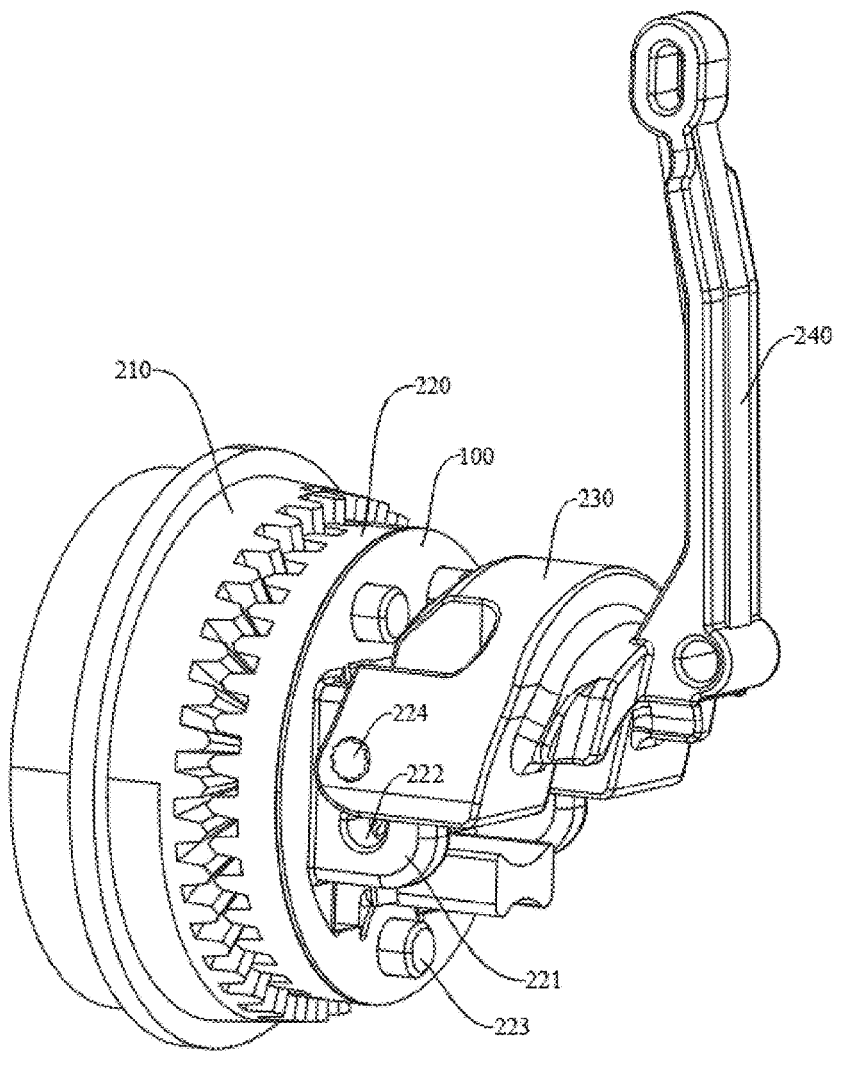
FIG. 4 is a structural schematic diagram of a self-locking device (with a rotating shaft hidden) according to the present disclosure.
Figure 5:
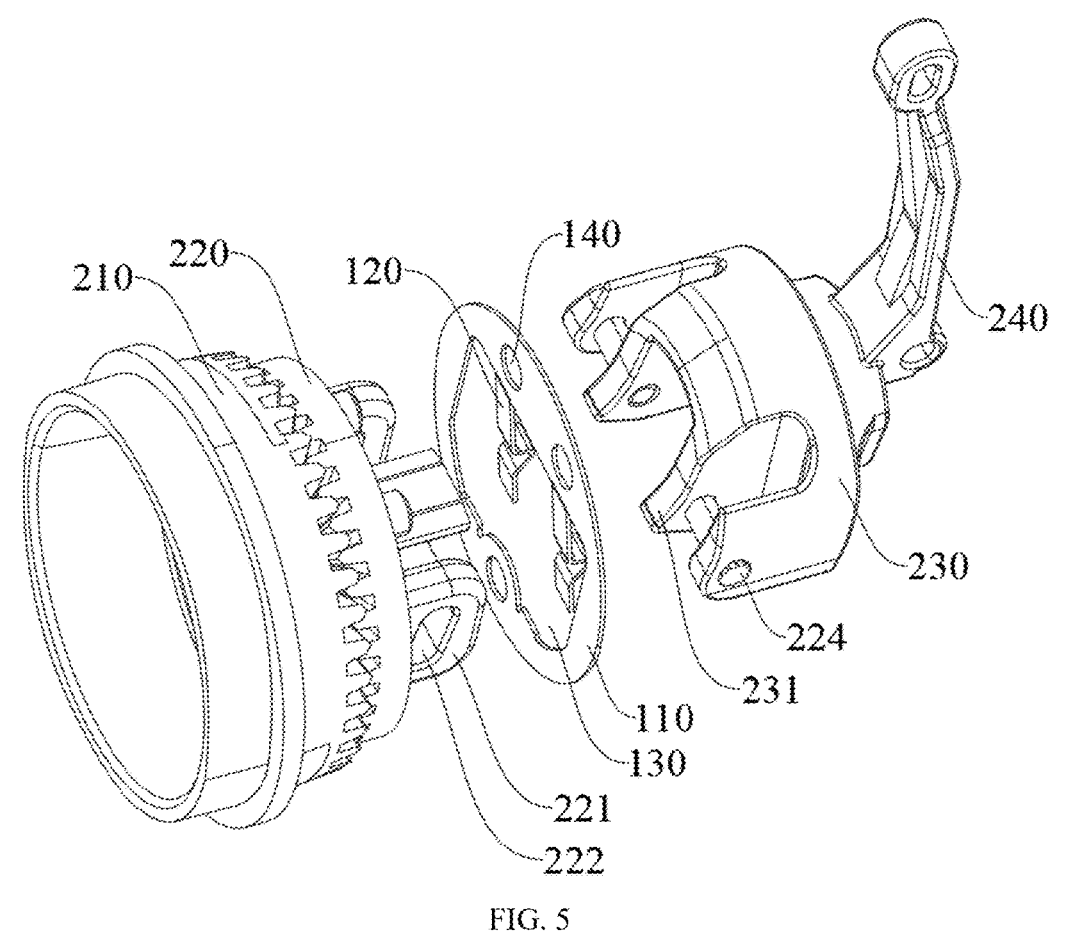
FIG. 5 is an exploded view of the self-locking device (with the rotating shaft hidden) according to the present disclosure.

This embodiment of the present disclosure provides control element 100 for an endoscope, including mounting base 110 and elastic member 120, as shown in FIG. 1 to FIG. 3. The mounting base 110 is provided with avoidance area 130. The avoidance area 130 is a hole or groove penetrating through the mounting base 110. The elastic member 120 is disposed corresponding to the avoidance area 130. One end of the elastic member 120 is connected to the mounting base 110, and the other end of the elastic member 120 is a free end. A projection of the elastic member 120 on a plane where the mounting base 110 is located covers a part of the avoidance area 130. The elastic member 120 is provided with first protrusion 121.

Existing self-locking devices for endoscopes generally use a leaf spring to assist in determining completion of switching control between locked and unlocked states. However, the leaf spring is constrained by its inherent structure (refer to the self-locking device for an endoscope disclosed in Chinese patent application CN111202488A). The two ends of the elastically deformable portion are connected to the leaf spring body, resulting in limited deformation amount of the elastically deformable portion. Therefore, during switching control between locked and unlocked states, the elastically deformable portion must be forced to generate a large deformation amount to complete the switching control. Nevertheless, for a leaf spring with a limited deformation amount, a greater deformation amount leads to an increased resistance. This causes an excessive resistance during state switching control by medical personnel, creating operational inconvenience. In this embodiment, the control element 100 corresponding to the leaf spring is improved by redesigning the deformable portion of the elastic member 120. One end of the elastic member 120 is connected to the mounting base 110, and the other end of the elastic member 120 is a free end. This design reduces constraints imposed by the mounting base 110 on the elastic member 120, thereby increasing the upper limit for the deformation amount of the elastic member 120 and reducing resistance corresponding to unit deformation amount. Meanwhile, the projection of the elastic member 120 on the plane where the mounting base 110 is located covers a part of the avoidance area 130, ensuring that the deformation space during deformation of the elastic member 120 is not restricted by the mounting base 110. The avoidance area 130 increases the deformation space for elastic deformation of the elastic member 120. When the elastic member 120 deforms elastically to the plane where the mounting base 110 is located, the mounting base 110 does not directly increase deformation resistance. This design further reduces resistance during elastic deformation of the elastic member 120, enabling medical personnel to easily and swiftly complete state switching control and enhancing operational convenience of the endoscope.

Figure 7:
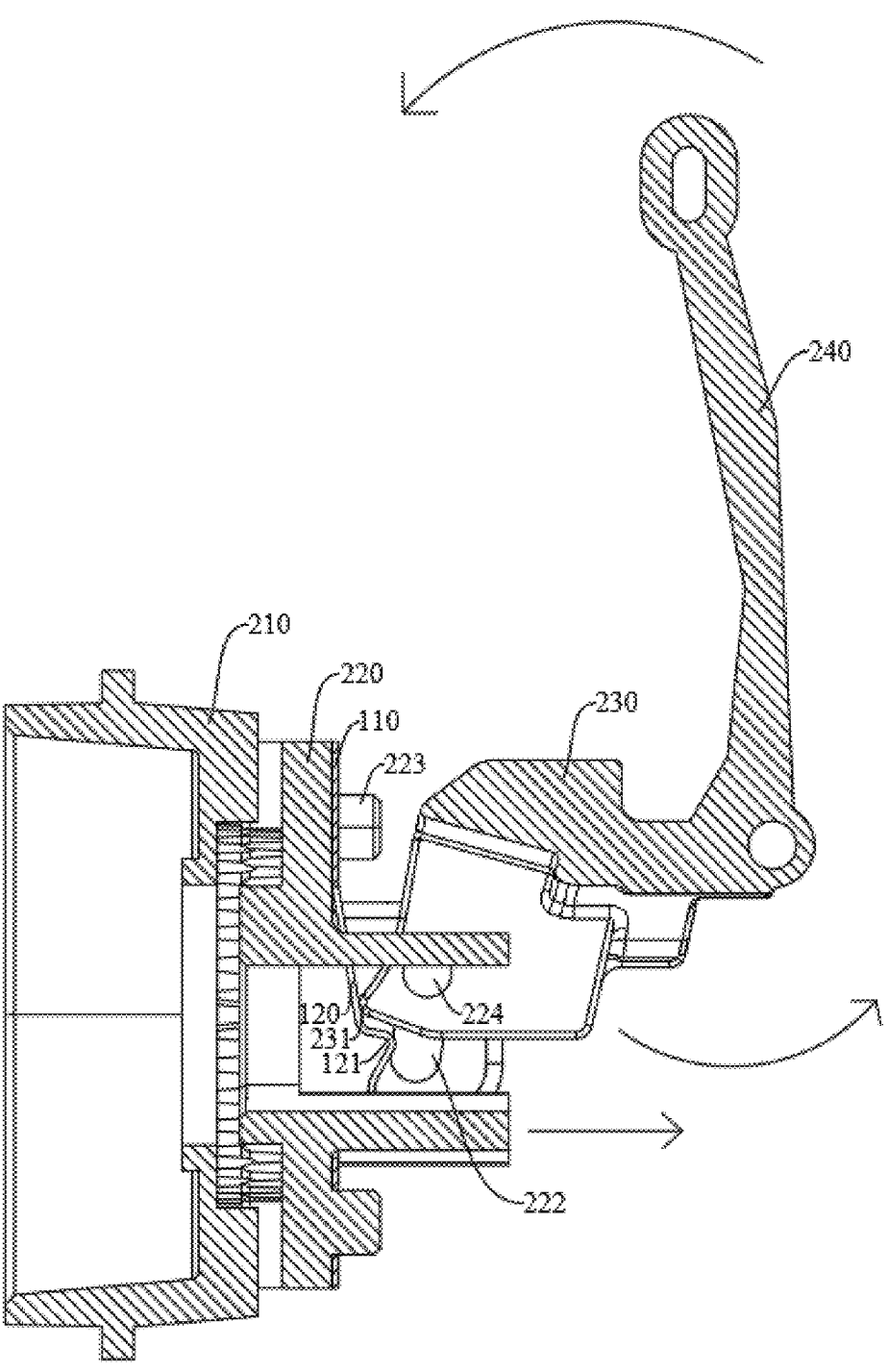
FIG. 7 is a sectional view of the self-locking device (with the rotating shaft hidden) according to the present disclosure.
Figure 8:
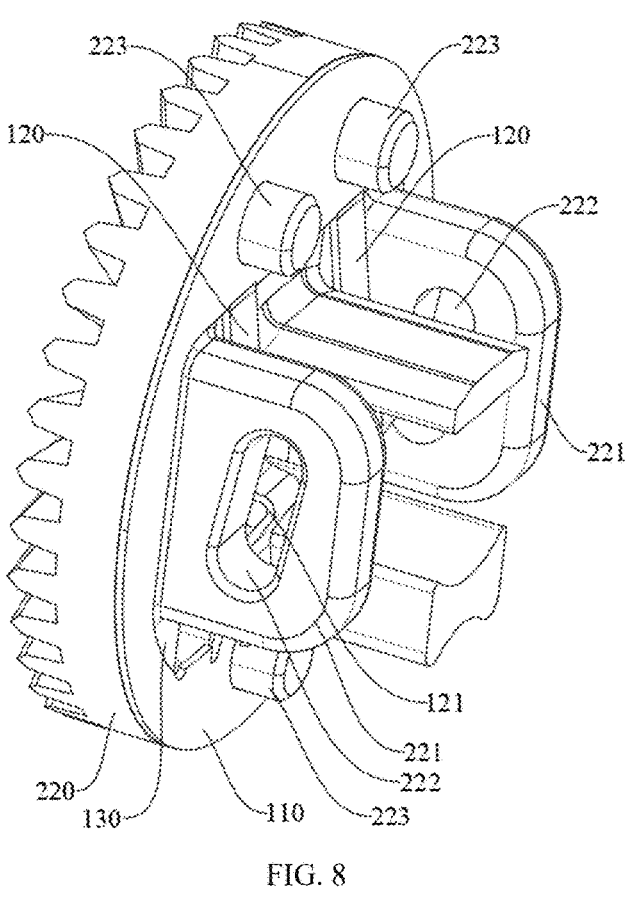
FIG. 8 is a structural schematic diagram of a driven gear and the control element according to the present disclosure.

Specifically, as shown in FIG. 1 and FIG. 3, the mounting base 110 is provided with mounting hole 140. As shown in FIG. 7 and FIG. 8, the mounting base 110 is provided with the mounting hole 140 to cooperate with mounting post 223 on driven gear 220, thereby facilitating quick mounting and fixation of the control element 100 to the driven gear 220. To improve mounting stability between the control element 100 and the driven gear 220, the number of mounting holes 140 on the mounting base 110 may be increased. That is, mounting holes 140 are respectively arranged at two sides of the avoidance area 130 to ensure connection stability between the control element 100 and the driven gear 220.

Specifically, the elastic member 120 is integrated with the mounting base 110. Preferably, the elastic member 120 and the mounting base 110 are formed by integral stamping of a metal sheet to improve manufacturing efficiency of the control element 100. In some embodiments, the elastic member 120 and the mounting base 110 may first be fabricated separately and then fixedly connected together.

Specifically, as shown in FIG. 3, the elastic member 120 includes first section 126 and second section 127. The second section 127 serves as the free end. The second section 127 is connected to the mounting base 110 via the first section 126. The first protrusion 121 is disposed on the second section 127. The first section 126 is located on an extension line of the second section 127. Alternatively, the first section 126 and the second section 127 form an L-shaped structure. The first protrusion 121 is disposed on the second section 127 away from the mounting base 110, and the projection of the elastic member 120 on the plane where the mounting base 110 is located covers a part of the avoidance area 130. Thus, the first protrusion 121 prominently protrudes from the plane where the mounting base 110 is located, enabling the first protrusion 121 and the elastic member 120 to more easily cooperate with limiting member 231 to achieve locking of a first positional state and a second positional state.

Specifically, the first protrusion 121 includes first inclined surface 1211 and second inclined surface 1212. The second inclined surface 1212 has a greater slope than the first inclined surface 1211. The second inclined surface 1212 is located between the first inclined surface 1211 and the first section 126. During mounting and use, the self-locking device for the endoscope includes the first positional state in a locked state and the second positional state in an unlocked state. In the locked state, the limiting member 231 is located on a side of the first inclined surface 1211 of the first protrusion 121. In the unlocked state, the limiting member 231 is located on a side of the second inclined surface 1212 of the first protrusion 121. Therefore, during switching between the unlocked state and the locked state, the smaller slope of the first inclined surface 1211 allows an operator to push the limiting member 231 over the first protrusion 121 with minimal thrust to complete the switching from the locked state to the unlocked state. This design prevents deformation damage to the elastic member 120 caused by the thrust on the elastic member 120 and compression by the mounting base 110, thereby extending service life of the device. During switching from the unlocked state to the locked state, the larger slope of the second inclined surface 1212 requires the operator to overcome greater resistance to push the limiting member 231 over the first protrusion 121. The passage of the limiting member 231 over the first protrusion 121 may provide clear tactile feedback to the operator. Meanwhile, since the side of the second inclined surface 1212 corresponds to the free end, forces applied to the elastic member 120 do not cause compression to the elastic member 120, ensuring operational safety of the elastic member 120.

Specifically, the second section 127 further includes first flat portion 1271 connected to the first inclined surface 1211 and second flat portion 1272 connected to the second inclined surface 1212. The first flat portion 1271 is connected to the first section 126. The arrangement of the first flat portion 1271 and the second flat portion 1272 at the two ends of the first protrusion 121 facilitates smooth positioning of the limiting member 231 during switching between the locked and unlocked state, improving operational comfort and convenience. In some embodiments, the second section 127 may be inclined to enhance state locking of the self-locking device. With reference to the plane where the mounting base 110 is located, the first flat portion 1271 is positioned at a high point and the second flat portion 1272 at a low point.

Specifically, the elastic member 120 further includes third section 128. One end of the second section is connected to the mounting base via the first section, and the other end of the second section is connected to the mounting base via the third section. The elastic member has a U-shaped structure. Since the driven gear 220 of the self-locking device is provided with protrusion 221, the U-shaped elastic member cooperates with the protrusion 221 to achieve rapid positioning and mounting between the control element and the driven gear 220. Through proper configuration, mutual limiting between the control element and the driven gear 220 is realized via a gap between the control element and the driven gear. Additionally, the second section 127 of the U-shaped structure serves as the free end and functions as a sliding track for the limiting member 231. This configuration also increases the upper limit for the deformation amount of the elastic member 120, reducing resistance when the limiting member 231 passes over the first protrusion 121, and enhancing operational convenience of the device.

In some embodiments, the first section 126 may further be provided with second protrusion 122. The second protrusion 122 increases elastic potential energy of the elastic member 120 to ensure control for the unlocked and locked states of the endoscope.

In some embodiments, the third section 128 may further be provided with third protrusion 123. The third protrusion 123 increases elastic potential energy of the elastic member 120 to ensure control for the unlocked and locked states of the endoscope.

Embodiment 2

This embodiment of the present disclosure provides a self-locking device for an endoscope, including driving gear 210, driven gear 220, flap 230, and the control element 100 in Embodiment 1, as shown in FIG. 4 to FIG. 11. The driven gear 220 is located between the driving gear 210 and the flap 230. The driving gear 210 and the driven gear 220 are coaxially arranged. The flap 230 is slidably connected to the driven gear 220. A sliding stroke between the flap 230 and the driven gear 220 includes a first positional state and a second positional state. In the first positional state, the driving gear 210 is separated from the driven gear 220. In the second positional state, the driving gear 210 is engaged with the driven gear 220. The control element 100 is disposed on a side wall of the driven gear 220 adjacent to the flap 230. The flap 230 is provided with limiting member 231. The limiting member 231 cooperates with the elastic member 120 to achieve locking of the first positional state and/or the second positional state.

Figure 6:
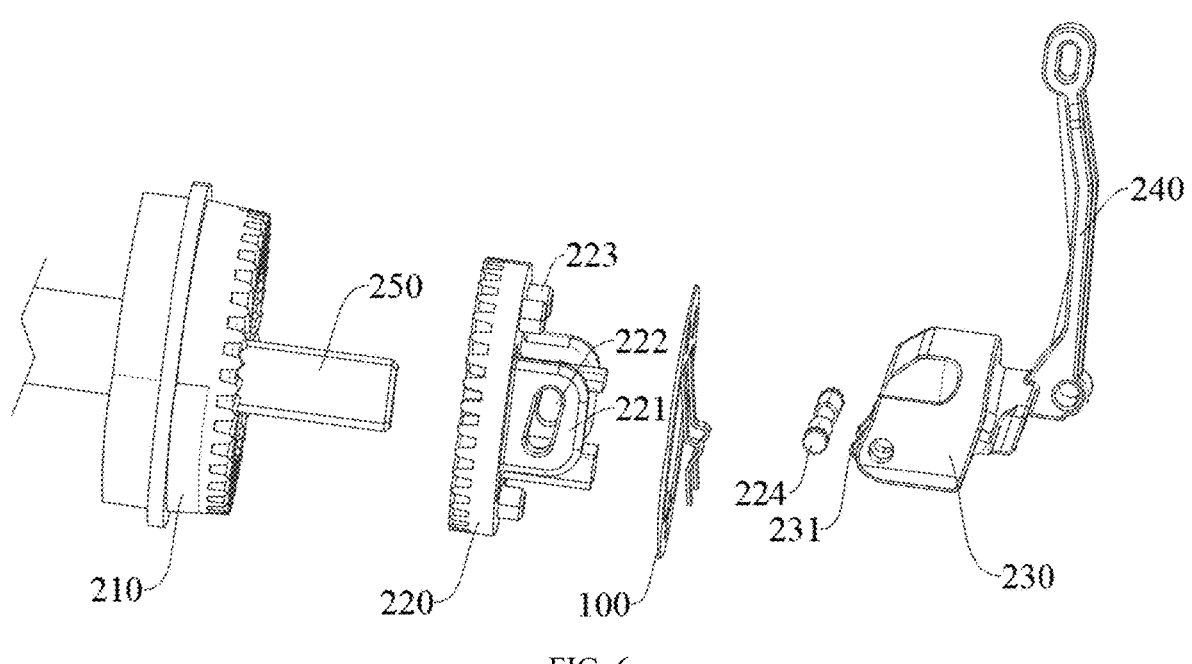
FIG. 6 is an exploded view of the self-locking device (with the rotating shaft shown) according to the present disclosure.

When controlling bending of an active bending section of the endoscope, the control of the active bending section is achieved by operating a traction wire. After the active bending section is bent into position, the state of the traction wire is controlled by the self-locking device to prevent accidental change in the state of the active bending section. In this embodiment, in the first positional state, the driving gear 210 is separated from the driven gear 220, preventing medical personnel from operating the traction wire via lever 240. At this time, the self-locking device is in the locked state. In the second positional state, the driving gear 210 is engaged with the driven gear 220. Medical personnel can drive rotation of the driving gear 210 via the lever 240, which is transmitted to the traction wire to achieve control thereof. At this time, the self-locking device is in the unlocked state. During switching control between the locked and unlocked states, the elastic member 120 exerts a thrust toward the flap 230 on the limiting member 231 under normal conditions, maintaining separation between the driving gear 210 and the driven gear 220. That is, the self-locking device remains in the first positional state under normal conditions. When switching to the unlocked state is required, as shown in FIG. 6, the flap 230 is pushed to generate sliding between the flap 230 and the driven gear 220, causing the flap 230 to overcome elastic resistance of the control element 100 and forcing the driven gear 220 to move axially toward the driving gear 210. When the limiting member 231 moves along the elastic member 120 to pass over the first protrusion 121, the driven gear 220 engages with the driving gear 210, completing the switching control from the locked state to the unlocked state. Additionally, by reversely moving the flap 230 to generate sliding between the flap 230 and the driven gear 220, the driven gear 220 is forced to move axially away from the driving gear 210. When the limiting member 231 moves along the elastic member 120 to pass over the first protrusion 121, the driven gear 220 separates from the driving gear 210, completing the switching control from the unlocked state to the locked state. During the state switching control, the self-locking device provides sufficient deformation space for the control element 100, effectively reducing resistance of the control element 100 during the process of state switching and improving operational convenience of the device.

In some embodiments, in the first positional state, the driving gear 210 is separated from the driven gear 220, and medical personnel can operate the traction wire via the lever 240. At this time, the self-locking device is in the locked state. In the second positional state, the driving gear 210 is engaged with the driven gear 220, and the traction wire is constrained by the driving gear 210 and thus cannot be operated. At this time, the self-locking device is in the unlocked state.

Specifically, the first protrusion 121 is configured to cooperate with the limiting member 231 to achieve locking of the first positional state. The limiting member 231 is configured to cooperate with the elastic member 120 to achieve locking of the second positional state. During state switching control, the elastic member 120 on the control element 100 continuously applies a thrust to the flap 230 to move it away from the driving gear 210. The axial relative position between the flap 230 and housing 40 is fixed, while the axial relative position between the driven gear 220 and the housing 40 is adjustable. Therefore, during switching control from the unlocked state to the locked state, when the limiting member 231 moves along the elastic member 120 to pass over the first protrusion 121, the first protrusion 121 imposes a positional constraint on the limiting member 231, which synergizes with the thrust applied by the elastic member 120 and the slidable connection between the flap 230 and the driven gear 220 to achieve locking of the first positional state. Thus, the relative positional relationship between the flap 230 and the driven gear 220, as well as between the driven gear 220 and the driving gear 210, remains locked. During switching control from the locked state to the unlocked state, the flap 230 is pushed to slide, causing synchronous displacement of the limiting member 231 along the elastic member 120. When the limiting member 231 moves to pass over the first protrusion 121, the first protrusion 121 no longer constrains the limiting member 231. Due to the continuous thrust of the elastic member 120, the self-locking device remains in the unlocked state. Furthermore, the abrupt resistance change caused by the first protrusion 121 during switching control provides direct feedback to medical personnel, generating a clear signal indicating whether operation is complete, thereby improving operational convenience of the device.

Figure 9:
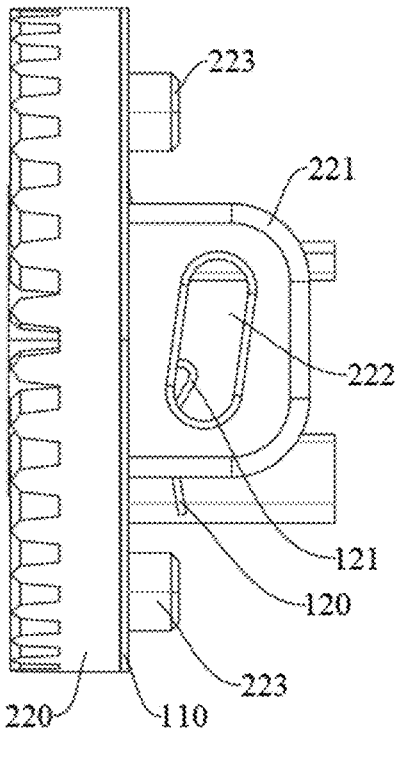
FIG. 9 is a side view of FIG. 8.
Figure 10:
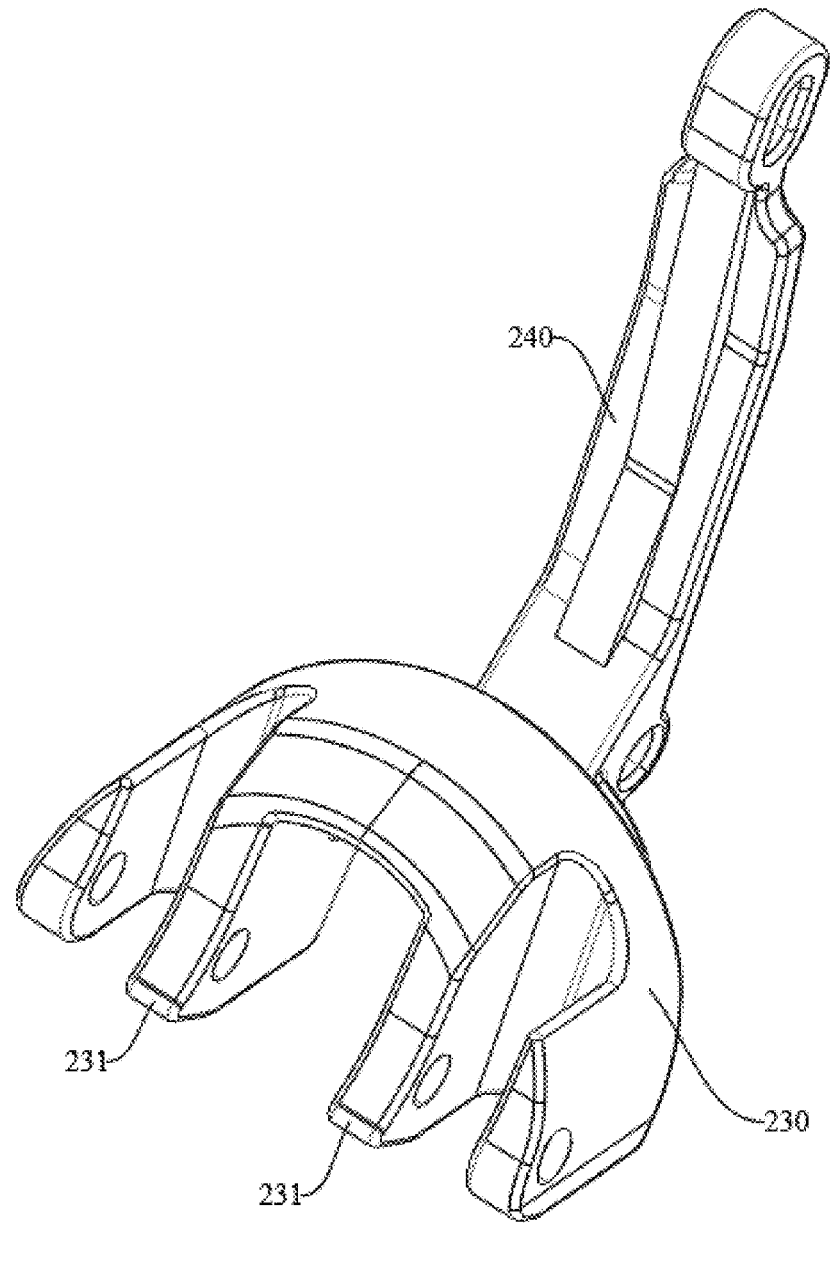
FIG. 10 is a structural schematic diagram of a flap and a lever that are connected.
Figure 11:
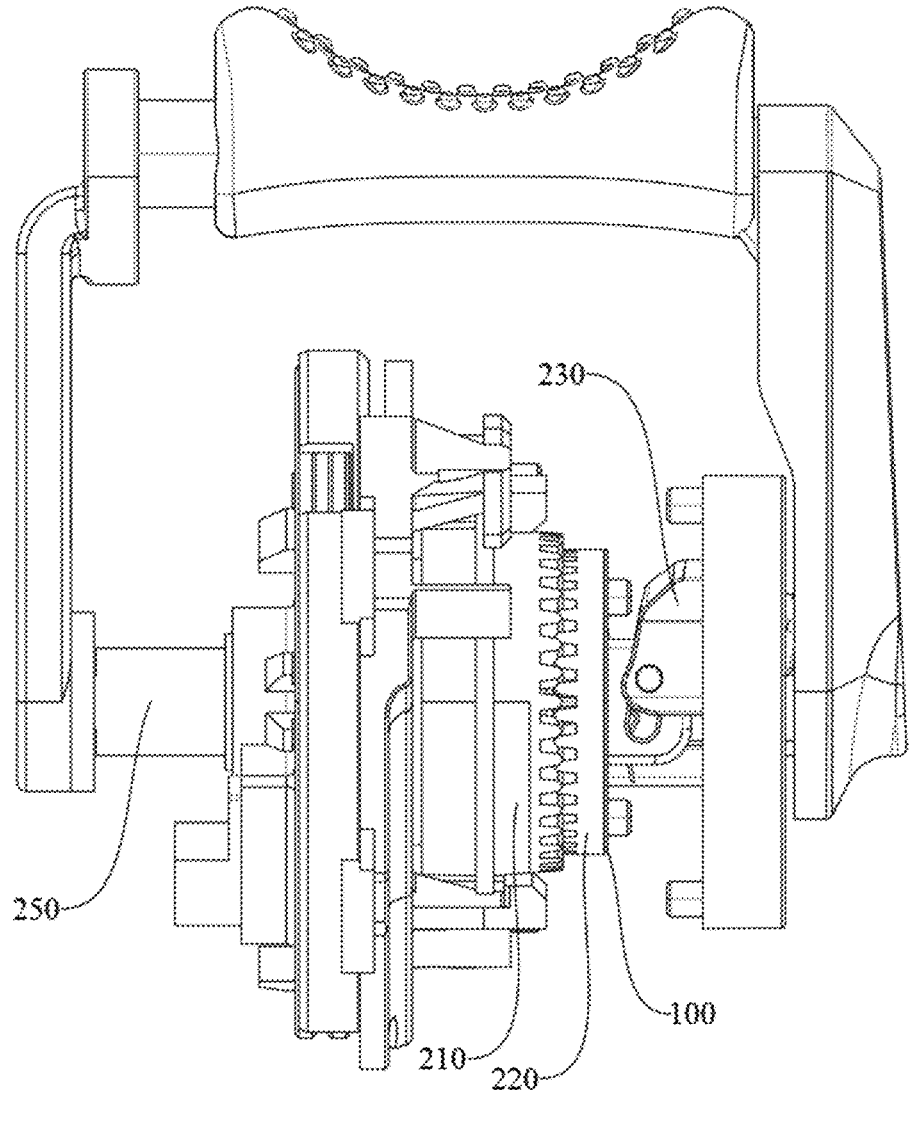
FIG. 11 is a diagram of the self-locking device in a use state according to the present disclosure.

Specifically, as shown in FIG. 6, FIG. 8, and FIG. 9, the driven gear 220 is provided with protrusion 221. The protrusion 221 is provided with sliding groove 222. Slider 224 matching the sliding groove 222 is disposed in the sliding groove 222. The slider 224 is connected to the flap 230. The driving gear 210 and the driven gear 220 are coaxially arranged on rotating shaft 250. The driven gear 220 is slidably connected to the rotating shaft 250 along an axial direction. The driving gear 210 is coaxially rotatably connected to the rotating shaft 250. An angle between the sliding groove 222 and a central axis of the rotating shaft 250 is acute. When the self-locking device is mounted in the endoscope, as shown in FIG. 11, the axial relative position between the flap 230 and the housing 40 is fixed, while the axial relative position between the driven gear 220 and the housing 40 is adjustable. Therefore, when the flap 230 is driven to rotate by overcoming resistance of the control element 100, rotational potential energy of the flap 230 is transmitted to the driven gear 220. This forces the driven gear 220 to move axially along the rotating shaft toward or away from the driving gear 210, thereby completing switching control between the locked and unlocked states by driving the flap 230. The acute angle between the sliding groove 222 and the central axis of the rotating shaft 250 efficiently converts the rotational potential energy of the flap 230 into axial kinetic energy of the driven gear 220.

Specifically, as shown in FIG. 8, the protrusion 221 is disposed on a side wall of the driven gear 220 adjacent to the flap 230, and the protrusion 221 passes through the avoidance area 130. Since the protrusion 221 passes through the avoidance area 130, the protrusion 221 can limit and fix the control element 100. Meanwhile, the space between the flap 230 and the driven gear 220 is fully utilized to achieve stable mounting of the self-locking device within a confined space.

Specifically, the side wall of the driven gear 220 adjacent to the flap 230 is provided with mounting post 223 matching with the mounting hole 140. When the self-locking device is mounted in the endoscope, the mounting hole 140 cooperates with the mounting post 223. This enables rapid positional positioning, mounting, and connection between the control element 100 and the driven gear 220, improving manufacturing convenience of the device.

Embodiment 3

Figure 12:
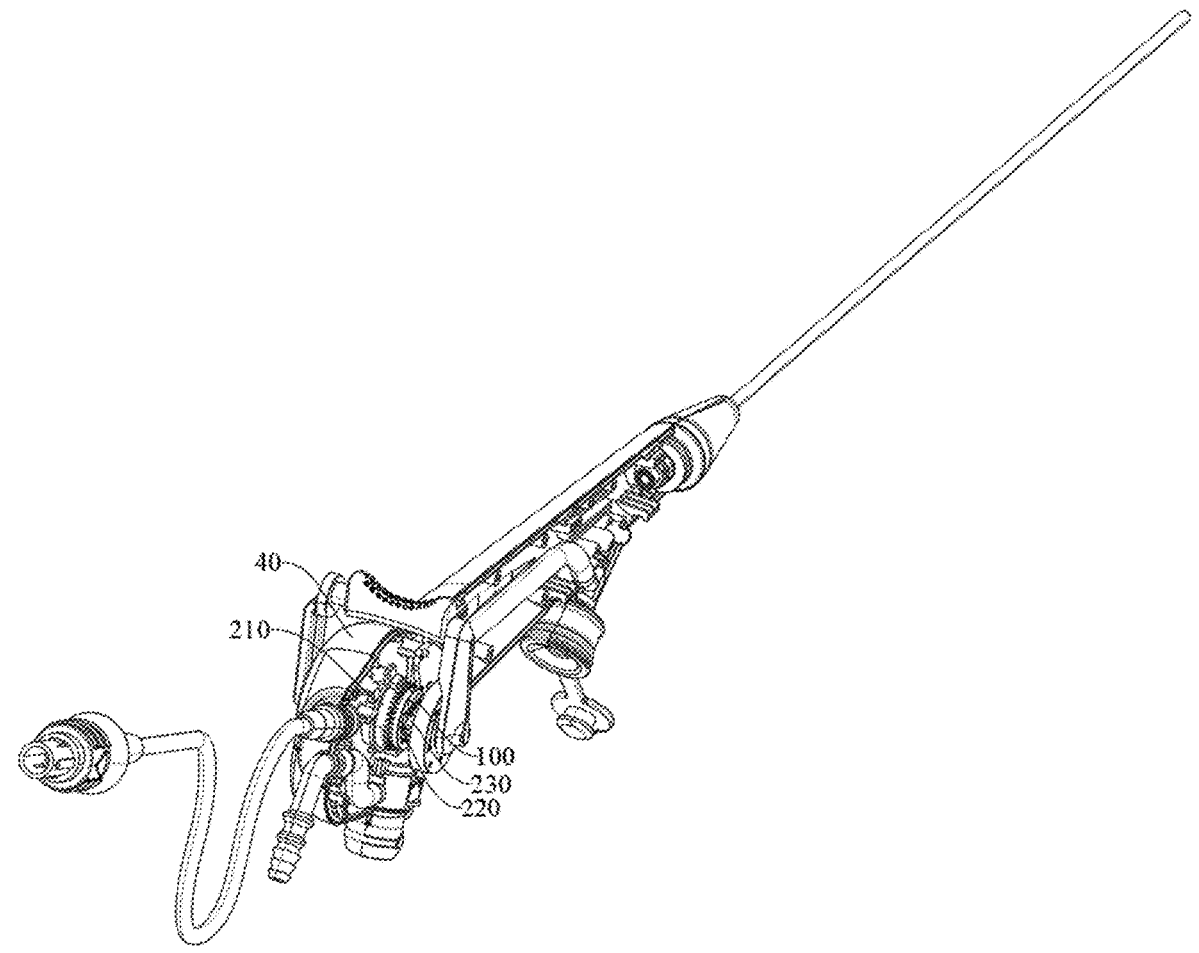
FIG. 12 is a structural schematic diagram for an endoscope according to the present disclosure.

This embodiment of the present disclosure provides a handle for an endoscope, including housing 40, a lever, and the self-locking device in Embodiment 2, as shown in FIG. 11 and FIG. 12. The driving gear 210 and the driven gear 220 are disposed inside the housing 40. The lever 240 is connected to the flap 230, and at least a portion of the lever 240 is disposed outside the housing 40. In this embodiment, preferably, the lever 240 and the flap 230 are configured as an L-shaped structure, and a connection end between the lever 240 and the flap 230 is pivotally connected to an inner wall of the housing. Thus, when the lever 240 is driven to rotate, the flap 230 rotates synchronously, facilitating state switching control of the self-locking device.

Embodiment 4

This embodiment of the present disclosure provides an endoscope, including the self-locking device in Embodiment 2 or the handle in Embodiment 3, as shown in FIG. 12. During use, when the flap 230 is driven to rotate in a state where the driving gear 210 is engaged with the driven gear 220, the driven gear 220 connected to the flap 230 rotates synchronously. Due to the meshing relationship, the driving gear 210 rotates synchronously with the driven gear 220. When the driving gear 210 rotates, it drives the rotating shaft 250 to rotate synchronously. As the rotating shaft 250 rotates, a traction wire on the rotating shaft 250 controls a turntable to rotate, so as to pull the traction wire to achieve bending control of the active bending section. In some embodiments, when the driving gear 210 is engaged with the driven gear 220, the rotation of the driven gear 220 is constrained to restrict the rotation of the turntable controlled by the traction wire on the rotating shaft 250. When the driving gear 210 is separated from the driven gear 220, the traction wire on the rotating shaft 250 is driven to control the turntable to rotate, so as to pull the traction wire to achieve bending control of the active bending section.

It should be noted that the endoscope in the embodiment of the present disclosure may be a bronchoscope, pyeloscope, esophagoscope, gastroscope, enteroscope, otoscope, nasoscope, oral endoscope, laryngoscope, colposcope, laparoscope, arthroscope, etc. The present disclosure imposes no specific limitations on the type of the endoscope.

The above are merely preferred embodiments of the present disclosure, and not intended to limit the present disclosure. Any modifications, equivalent replacements, and improvements made within the spirit and principle of the present disclosure should fall within the protection scope of the present disclosure.

The invention claimed is:

1. A control element for an endoscope, comprising a mounting base and an elastic member, wherein the mounting base is provided with an avoidance area; the avoidance area is a hole or groove penetrating through the mounting base; the elastic member is disposed corresponding to the avoidance area; a first end of the elastic member is connected to the mounting base, and a second end of the elastic member is a free end; a projection of the elastic member on a plane where the mounting base is located covers a part of the avoidance area; the elastic member is provided with a first protrusion; the elastic member comprises a first section, a second section and a third section; the second section serves as the free end; a first end of the second section is connected to the mounting base via the first section, and a second end of the second section is connected to the mounting base via the third section; and the elastic member has a U-shaped structure, wherein the first protrusion comprises a first inclined surface and a second inclined surface; the second inclined surface has a greater slope than the first inclined surface; and the second inclined surface is located between the first inclined surface and the first section.

2. The control element according to claim 1, wherein the mounting base is provided with a mounting hole; and/or the elastic member is integrated with the mounting base.

3. The control element according to claim 1, wherein the second section further comprises a first flat portion connected to the first inclined surface and a second flat portion connected to the second inclined surface; and the first flat portion is connected to the first section.

4. The control element according to claim 1, wherein the first section is provided with a second protrusion; and/or the third section is provided with a third protrusion.

5. A self-locking device for an endoscope, comprising a driving gear, a driven gear, a flap, and the control element according to claim 1, wherein the driven gear is located between the driving gear and the flap; the driving gear and the driven gear are coaxially arranged; the flap is slidably connected to the driven gear; a sliding stroke between the flap and the driven gear comprises a first positional state and a second positional state; in the first positional state, the driving gear is separated from the driven gear; in the second positional state, the driving gear is engaged with the driven gear; the control element is disposed on a side wall of the driven gear adjacent to the flap; the flap is provided with a limiting member; and the limiting member is configured to cooperate with the elastic member to achieve locking of the first positional state and/or the second positional state.

6. A handle for an endoscope, comprising a housing, a lever, and the self-locking device according to claim 5, wherein the driving gear and the driven gear are disposed inside the housing; the lever is connected to the flap; and at least a portion of the lever is disposed outside the housing.

7. An endoscope, comprising the self-locking device according to claim 5.

8. The self-locking device according to claim 5, wherein in the control element, the mounting base is provided with a mounting hole; and/or the elastic member is integrated with the mounting base.

9. The self-locking device according to claim 5, wherein in the control element, the first protrusion comprises a first inclined surface and a second inclined surface; the second inclined surface has a greater slope than the first inclined surface; and the second inclined surface is located between the first inclined surface and the first section.

10. The self-locking device according to claim 9, wherein in the control element, the second section further comprises a first flat portion connected to the first inclined surface and a second flat portion connected to the second inclined surface; and the first flat portion is connected to the first section.

11. The self-locking device according to claim 5, wherein in the control element, the first section is provided with a second protrusion; and/or the third section is provided with a third protrusion.

12. An endoscope, comprising the handle according to claim 6.

* * * * *